(12) United States Patent
Barreto Caban et al.

(10) Patent No.: US 10,071,353 B2
(45) Date of Patent: Sep. 11, 2018

(54) AQUEOUS DISPERSANT FORMULATION

(71) Applicant: Hewlett-Packard Development Company, L.P., Houston, TX (US)

(72) Inventors: Marcos A. Barreto Caban, Aguadilla, PR (US); Thomas W. Butler, San Diego, CA (US); Rodney David Stramel, San Diego, CA (US); Gregg A. Lane, San Diego, CA (US)

(73) Assignee: Hewlett-Packard Development Company, L.P., Houston, TX (US)

(*) Notice: Subject to any disclaimer, the term of this patent is extended or adjusted under 35 U.S.C. 154(b) by 0 days.

(21) Appl. No.: 15/543,194

(22) PCT Filed: Jan. 29, 2015

(86) PCT No.: PCT/US2015/013585
§ 371 (c)(1),
(2) Date: Jul. 12, 2017

(87) PCT Pub. No.: WO2016/122541
PCT Pub. Date: Aug. 4, 2016

(65) Prior Publication Data
US 2017/0361290 A1    Dec. 21, 2017

(51) Int. Cl.
*B41M 5/28* (2006.01)
*C07D 495/00* (2006.01)
(Continued)

(52) U.S. Cl.
CPC ........ *B01F 17/0028* (2013.01); *C07D 335/10* (2013.01); *C07D 335/16* (2013.01); *C08F 226/00* (2013.01); *C09D 11/38* (2013.01)

(58) Field of Classification Search
CPC ... C09D 11/38; B01F 17/0028; C07D 335/10; C07D 335/16; C08F 226/00
(Continued)

(56) References Cited

U.S. PATENT DOCUMENTS

| 4,459,416 A | 7/1984 | Curtis et al. |
| 6,790,875 B2 | 9/2004 | Noguchi et al. |

(Continued)

FOREIGN PATENT DOCUMENTS

| CN | 1472233 | 2/2004 |
| EP | 2161264 | 3/2010 |

(Continued)

OTHER PUBLICATIONS

Corrales T et al "Novel water soluble copolymers based on thioxanthone: photochemistry and photoinitiation activity", Jrnl of Photochem. & Photobio. A: Chem. 169, 2005, 95-100.

(Continued)

*Primary Examiner* — William K Cheung
(74) *Attorney, Agent, or Firm* — Dierker & Kavanaugh PC (57) ABSTRACT

An aqueous radiation curable dispersant formulation includes water and styrene acrylic resin stabilized thioxanthone derivative photoinitiator particles dispersed in the water. The styrene acrylic resin stabilized thioxanthone derivative photo initiator particles have a volume-weighted mean diameter of less than 40 nm. The styrene acrylic resin stabilized thioxanthone derivative photo initiator particles include a water-insoluble, thioxanthone derivative photoinitiator core having one, two, or three units. When the water-insoluble, thioxanthone derivative photoinitiator core includes two units or three units, the units are covalently bonded together.

15 Claims, 3 Drawing Sheets

(51) Int. Cl.
  *B01F 17/00*  (2006.01)
  *C09D 11/38*  (2014.01)
  *C07D 335/10*  (2006.01)
  *C07D 335/16*  (2006.01)
  *C08F 226/00*  (2006.01)

(58) Field of Classification Search
  USPC .............................................. 522/53; 549/27
  See application file for complete search history.

(56) References Cited

U.S. PATENT DOCUMENTS

| | | |
|---|---|---|
| 8,378,002 B2 | 2/2013 | Kyota |
| 8,511,812 B2 | 8/2013 | Kuwabara et al. |
| 2004/0209976 A1 | 10/2004 | Nakhmanovich et al. |
| 2011/0195198 A1* | 8/2011 | Loccufier ................ C07C 69/76 427/532 |

FOREIGN PATENT DOCUMENTS

| | | |
|---|---|---|
| KR | 1020130111582 | 10/2013 |
| WO | WO 1997/049664 | 12/1997 |

OTHER PUBLICATIONS

International Search Report and Written Opinion for International Application No. PCT/US2015/013585 dated Sep. 14, 2015, 9 pages.

Qiu, J. et al., "Water-Soluble and Polymerizable Thioxanthone Photoinitiator Containing Imidazole", Journal of Applied Polymer Science, 2014, vol. 131, No. 16, pp. 40659(1-6).

* cited by examiner

$$M_V = \frac{\sum_1^n D_i^4}{\sum_1^n D_i^3}$$

AQUEOUS DISPERSANT FORMULATION

BACKGROUND

In addition to home and office usage, inkjet technology has been expanded to high-speed, commercial and industrial printing. Inkjet printing is a non-impact printing method that utilizes electronic signals to control and direct droplets or a stream of ink to be deposited on media. Some commercial and industrial inkjet printers utilize fixed printheads and a moving substrate web in order to achieve high speed printing. Current inkjet printing technology involves forcing the ink drops through small nozzles by thermal ejection, piezoelectric pressure or oscillation onto the surface of the media.

Some printing processes incorporate drying, or curing using energy curable systems. Energy curable systems are utilized, for example, when the inkjet ink includes a curable binder and a photoinitiator. The photoinitiator absorbs radiation and produces a primary radical species to initiate polymerization of the curable binder(s) in the inkjet ink.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Inkjet inks that include curable components (e.g., monomer(s), binder(s), etc.) and photoinitiators often include organic solvent(s), in part because this type of solvent is fast drying. The organic solvent partially or fully evaporates in a short amount of time after being printed, leaving the other ink components in the form of a dried film on the print medium/substrate. While organic solvent(s) have advantages, many inkjet inks are water based.

In contrast, most commercially available photoinitiators are not water soluble or water dispersible, and thus are not suitable for water based inks. Rather, a majority of the available photoinitiators are soluble in the monomer(s) that is/are to be cured. These photoinitiators are commonly used in non-aqueous inkjet inks that include the monomer. In addition to the non-compatibility with water, many of these photoinitiators have an undesirable odor and/or may migrate in the cured material.

The inventors of the present disclosure have unexpectedly and fortuitously discovered an aqueous dispersant formulation that includes styrene acrylic resin stabilized thioxanthone derivative photoinitiator particles, which are both dispersible and stable in the aqueous formulation. These resin stabilized particles are considered adsorbed particles, in part because the styrene acrylic resin associates (or adsorbs) with the surface of the thioxanthone derivative photoinitiator while also arranging the adsorbed particles within the aqueous formulation.

The inventors have also discovered a method for preparing the aqueous dispersant formulation. The method advantageously transforms an initial water-insoluble thioxanthone derivative photoinitiator into styrene acrylic resin stabilized, water dispersible thioxanthone derivative photoinitiator particles having a volume-weighted mean diameter of less than 40 nm. The volume-weighted mean diameter of the particles may contribute to the advantageous characteristics exhibited by the aqueous dispersant formulation, including water dispersibility and transparency. Both the water dispersibility and the transparency of the formulation are unexpected properties, in part because the initial water-insoluble photoinitiator is not only water-insoluble, but also has a consistency that resembles tree sap, and has a dark color. These unexpected properties of examples of the aqueous dispersant formulation render the aqueous dispersant formulation(s) suitable for use in aqueous inkjet inks. Furthermore, with the transformed water-insoluble photoinitiator (i.e., the styrene acrylic resin stabilized, thioxanthone derivative photoinitiator particles), examples of the aqueous dispersant formulation also exhibit low odor and low migration in cured materials formed from an ink including the dispersant formulation.

Examples of the styrene acrylic resin stabilized thioxanthone derivative photoinitiator particles include a particular styrene acrylic resin. In an example, the styrene acrylic resin has an acid number (e.g., mg KOH per 1 gram of polymer) that is greater than or equal to 100 and a molecular weight that is greater than or equal to 4500 g/mol. The styrene acrylic resin is water soluble and contributes to the stability of the particles that are formed, and thus to the stability of the final aqueous dispersant formulation.

In a colloidal system, stability may be due to electrostatic stabilization and/or steric stabilization. Electrostatic stabilization is a charge based stabilization relying on charged particles interacting in a vehicle/carrier. Steric stabilization uses spatial hindrance driven by energies of polymer chain repulsion. Electro-steric stabilization is a hybrid of electrostatic and steric stabilization. In the method disclosed herein, stabilization is achieved by breaking the initial water-insoluble thioxanthone derivative photoinitiator into smaller units (which exposes new surface(s) of the photoinitiator), and inserting the styrene acrylic resin on the new surface(s). This advantageously prevents the smaller units of the water-insoluble thioxanthone derivative photoinitiator from agglomerating. The interactions are dynamic, in that new surfaces are constantly refreshed and exposed to the styrene acrylic resin. The interactions between the water-insoluble thioxanthone derivative photoinitiator and the styrene acrylic resin and between the resin and water may rely on steric hindrance and/or charge, and thus the particles and overall formulation may be stabilized by electrostatic stabilization and/or steric stabilization.

Figures 1A, 1B:
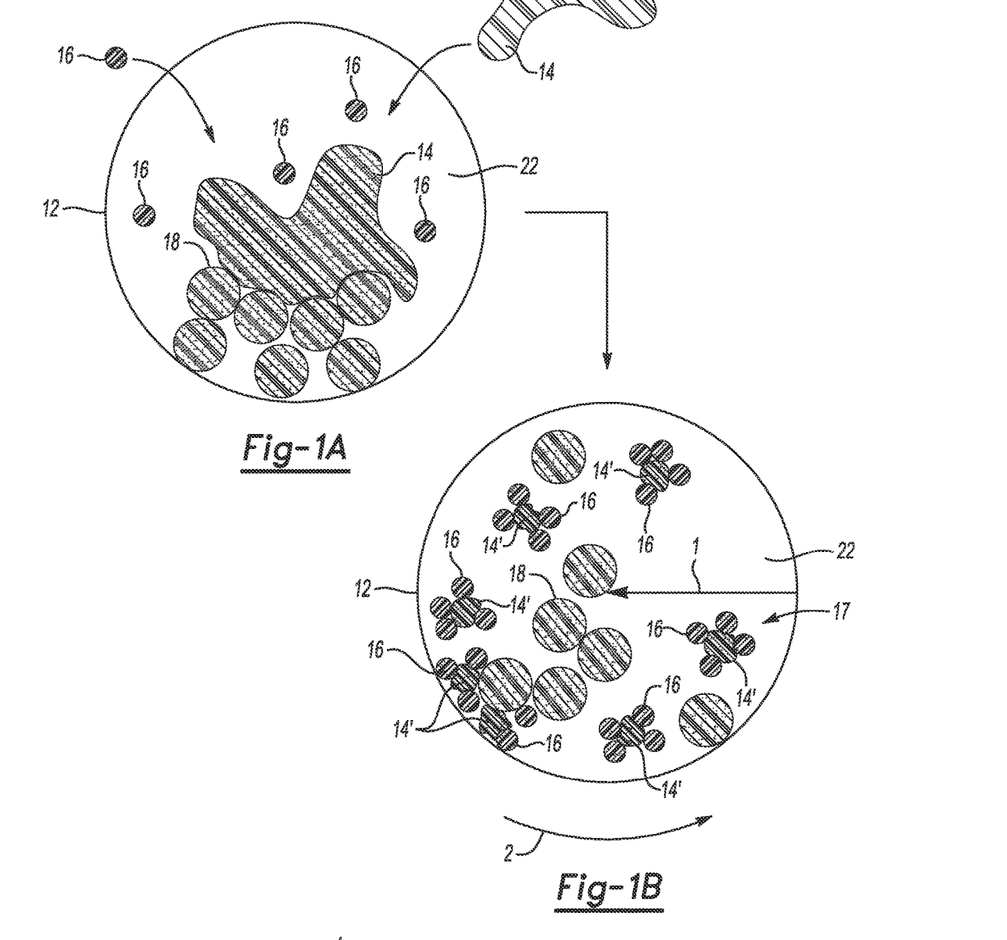
FIGS. 1A-1B are schematic, top and partially cross-sectional views of an example of a method for forming an aqueous dispersant formulation.

An example of a method for manufacturing the aqueous dispersant formulation is shown in FIGS. 1A-1B. The final aqueous dispersant formulation (depicted in FIG. 1B) includes styrene acrylic resin stabilized thioxanthone derivative photoinitiator particles 17 having a volume-weighted mean diameter of less than 40 nm, and a balance of water 22. In some examples, the aqueous dispersant formulation includes only these components, with no additional compo- nents. In other instances, the aqueous dispersant formulation may also include, in addition to the components mentioned above, another polymeric dispersant, a co-solvent, or a combination thereof.

Turning to FIG. 1A, in this example of the method for forming the aqueous dispersant formulation, a mixture may be formed. In this example, the mixture includes an initial water-insoluble thioxanthone derivative photoinitiator 14, which is a precursor of the water dispersible thioxanthone derivative photoinitiator core 14'. The water dispersible thioxanthone derivative photoinitiator core 14' makes up the center portion of the styrene acrylic resin stabilized thioxanthone derivative photoinitiator particles 17 that are ultimately formed. The mixture also includes a styrene acrylic resin 16 and a balance of water 22. It is to be understood that, while not shown in FIGS. 1A-1B, in some instances, the additional components, such as the other polymeric dispersant and/or the co-solvent, may also be added to the mixture. Each of the mixture components will now be described.

The initial thioxanthone derivative photoinitiator 14 is a water-insoluble photoinitiator that has a thick tree sap-like consistency. The viscosity (at 25° C.) of the initial thioxanthone derivative photoinitiator 14 ranges from about 100,000 mPa*s (or cP) to about 250,000 mPa*s (or cP). The Heating of the initial thioxanthone derivative photoinitiator 14 may take place prior to forming the mixture. In an example, each of the mixture components may be heated to a temperature ranging from about 40° C. to about 60° C. prior to forming the mixture. For example, the initial thioxanthone derivative photoinitiator 14 may be heated, and then added to the other mixture components (e.g., the styrene acrylic resin 16 and the water 22). In this example, the styrene acrylic resin 16 and the water 22 may be mixed separately from the initial thioxanthone derivative photoinitiator 14. In this example, the styrene acrylic resin 16 and the water 22 may also be heated to the temperature ranging from about 40° C. to about 60° C. In another example, each of the initial thioxanthone derivative photoinitiator 14, the styrene acrylic resin 16, and the water 22 may be heated separately and then added together. In still another example, the initial thioxanthone derivative photoinitiator 14 may be heated, and then added to the other mixture components (e.g., the styrene acrylic resin 16 and the water 22), which have not been heated.

The initial thioxanthone derivative photoinitiator 14 and the thioxanthone derivative photoinitiator core 14' (i.e., the initiator before and after milling) include one, two, and/or three units, where one unit is defined by the following structure (I):

particles within the initial thioxanthone derivative photoinitiator 14 may be relatively large, having an average particle size of 130 nm or greater. The average particle size may be measured using dynamic light scatting in a pre-mixed solution of the initial photoinitiator 14. The consistency, viscosity, and particle size and/or volume-weighted mean diameter of the initial thioxanthone derivative photoinitiator 14 are generally not suitable for use in aqueous inkjet inks or in milling techniques. However, the inventors have found that using the method(s) disclosed herein, the initial thioxanthone derivative photoinitiator 14 can be added to the mixture and milled to form the thioxanthone derivative photoinitiator core 14', which is dispersed within the aqueous dispersant formulation by the styrene acrylic resin 16 adsorbed thereon.

In an example of the method, the initial thioxanthone derivative photoinitiator 14 may be heated to a temperature ranging from about 40° C. to about 60° C. In an example, the initial thioxanthone derivative photoinitiator 14 may be heated to a temperature of about 50° C. It has been found that heating the initial thioxanthone derivative photoinitiator 14 reduces the viscosity and thins the consistency, which renders it more suitable for milling processing. In an example, the viscosity of the initial thioxanthone derivative photoinitiator 14 may be reduced from the initial viscosity (i.e., from about 100,000 mPa*s (or cP) to about 250,000 mPa*s (or cP)) to a viscosity equal to or less than 1000 cP. For example, the reduced viscosity may range from about 500 cP to about 1000 cP.

where x=2-12. It is to be understood that when two or three subunits of structure (I) are included in the initial thioxanthone derivative photoinitiator 14 and/or the thioxanthone derivative photoinitiator core 14', the two or three subunits are covalently bonded together. In these examples, the units are covalently bound together through the carbon at the end of the carbon chain that is opposed to the end that is attached to the thioxanthone group (i.e., the carbon in the methyl group shown in structure (I)). A commercially available example of the initial thioxanthone derivative photoinitiator 14 includes GENOPOL*® TX-1 (made available by Rahn USA Corporation). The initial thioxanthone derivative photoinitiator 14 may be present in the mixture in an amount ranging from about 5 wt % to about 20 wt % based on the total wt % of the mixture.

The styrene acrylic resin 16 may also be used in the mixture, so that it is incorporated into the particle system of the aqueous dispersant formulation. As discussed herein, the styrene acrylic resin 16 disperses the thioxanthone derivative photoinitiator cores 14' in the water 22. The styrene acrylic resin 16 may be present in the mixture in an amount ranging from about 1 wt % active to about 10 wt % active based on the total wt % of the mixture. This weight percentage accounts for the weight percent of active styrene acrylic resin present in the mixture, and does not account for the total weight percent of a dispersant including the styrene acrylic resin 16 as a component. For example, the dispersant may be a 10% solution of the styrene acrylic resin 16 in water, and thus 85 wt % of the dispersant would include 8.5 wt % of active styrene acrylic resin 16.

Any suitable styrene acrylic resin that has an acid number greater than or equal to 100 and a molecular weight greater than or equal to 4500 g/mol may be used. Some commercially available examples of the styrene acrylic resin 16 include JONCRYL® 680, JONCRYL® 690, JONCRYL® 683, JONCRYL® HPD 296, JONCRYL® HPD 671, and JONCRYL® 678 (all made available by BASF Corporation).

In some instances, another polymeric dispersant (not shown in FIGS. 1A-1B) may be used in the mixture that is used to form the aqueous dispersant formulation. The other polymeric dispersant may also help to disperse the thioxanthone derivative photoinitiator cores 14' in the water 22. The other polymeric dispersant may be present in an amount ranging from 0 wt % to about 25 wt % based on the total wt % of the mixture. It is to be understood that the other polymeric dispersant may be 100% active. When the other polymeric dispersant is 100% active, the weight percent range provided for the other polymeric dispersant accounts for the total weight percent of the polymeric dispersant that is included. When the other polymeric dispersant is less than 100% active, the weight percent range provided for the other polymeric dispersant may be adjusted to account for the percentage that is active.

An example of the other polymeric dispersant includes a 100% active alkylphenol ethoxylate (APE) free polymeric dispersant, such as SOLSPERSE® 27000. The other polymeric dispersant may be a 100% active polymeric dispersant, such as SOLSPERSE® 21000. The other polymeric dispersant may be 50% active and APE free, for example SOLSPERSE® 46000 (all three of the SOLSPERSE® polymeric dispersants are made available by Lubrizol). At least some of the SOLSPERSE® dispersants are polyethylene glycol b-naphthyl ethers. Some additional examples of the other polymeric dispersant include SURFYNOL® 104 (an acetylenic diol surface active agent) and CARBOWET® GA-211 (a.k.a., SURFYNOL® CT-211, non-ionic, alkylphenylethoxylate and solvent free) (both of which are made available by Air Products and Chemicals). Still some further examples include AEROSOL® OT (sodium dioctyl sulfosuccinate made available by Cytec), DISPERBYK® 190 (a high molecular weight block copolymer with pigment affinic groups), and DISPERBYK® 199 (solution of a copolymer with pigment-affinic groups) (both DISPERBYK® dispersants are made available by BYK USA Inc.).

It is to be understood that combinations of any of the listed styrene acrylic resin 16 and/or other polymeric dispersants may be used. For examples, two different styrene acrylic resins 16 may be used together, or a styrene acrylic resin 16 may be used with any one or more of the other polymeric dispersants.

In some instances, a co-solvent (not shown in FIGS. 1A-1B) may be used in the mixture in addition to water (which is the main solvent). The co-solvent may help stabilize the initial thioxanthone derivative photoinitiator 14 (and the water dispersible thioxanthone derivative photoinitiator core 14') in the water 22. The co-solvent may be present in an amount ranging from 0 wt % to about 15 wt % based on the total wt % of the mixture.

Some examples of the co-solvent may be 1-(2-hydroxyethyl)-2-pyrrolidone, 2-methyl-1,3-propanediol, 2-pyrrolidinone, dipropylene glycol methyl ether acetate (DPMA), and combinations thereof.

As mentioned above, at least the initial thioxanthone derivative photoinitiator 14 is heated prior to preparing the mixture. To prepare the mixture, the components are then combined together. In an example of the method, the heated initial thioxanthone derivative photoinitiator 14 may be poured into a combination of the other mixture components, which may or may not have been heated. In another example of the method, a combination of the other mixture components (which may or may not have been heated) may be poured into the heated initial thioxanthone derivative photoinitiator 14.

In an example, the mixture may be formed by adding the components to a container or directly to a bead mill mixer 12, as shown from the top view in FIG. 1A. If the mixture is prepared in a container, any suitable container may be used. In this example, the mixture may be agitated in the container, and added to the bead mill mixer 12 along with a suitable grinding medium 18. If the mixture is prepared directly in the bead mill mixer 12, the bead mill mixer 12 may be any suitable bead mill mixer. In an example, the bead mill mixer 12 may be a Disperser DAS® 200 made by Lau, Kotobuki UAM series mills, EMI Mini Series mills, and any other small media capable bead mills. The grinding medium 18 may be introduced into the bead mill mixer 12 before or after the mixture. The grinding medium 18 may have a size ranging from about 0.05 mm to about 1.0 mm. An example of a suitable grinding medium 18 is 0.65 mm YTZ (yttria stabilized zirconia ceramic) beads.

Referring now to FIG. 1B, after the formation of the mixture, the mixture may be subjected to bead milling until the initial thioxanthone derivative photoinitiator 14 has been processed, and the styrene acrylic resin stabilized thioxanthone derivative photoinitiator particles 17 are formed. The broken up thioxanthone derivative photoinitiator cores 14' form the center portion of the styrene acrylic resin stabilized thioxanthone derivative photoinitiator particles 17, and the styrene acrylic resin (and other polymeric resin if present) adsorb to this center portion. The styrene acrylic resin stabilized thioxanthone derivative photoinitiator particles 17 have a volume-weighted mean diameter of less than 40 nm.

In an example, the bead milling of the mixture may be performed for a time ranging from about 0.5 hours to about 1.5 hours to form the styrene acrylic resin stabilized thioxanthone derivative photoinitiator particles 17. In this example of the method, to determine whether the aqueous formulation has been formed, the volume-weighted mean diameter of thioxanthone derivative photoinitiator 14 as it transforms into the cores 14' may be monitored during bead milling.

As shown in FIG. 1B, the bead mill mixer 12 applies several forces, such as a centripetal force (shown as "1" in FIG. 1B) and a rotational force (shown as "2" in FIG. 1B), in order to increase the movement of the grinding medium 18, which collides with the mixture components to create shear and reduce agglomerates of the thioxanthone derivative photoinitiator 14. In particular, the grinding medium 18 collides with the initial thioxanthone derivative photoinitiator 14, which causes breakage and thus reduces the volume-weighted mean diameter of the photoinitiator (i.e., transforming from agglomerates of photoinitiator 14 to core particles 14').

The photoinitiator 14 breakage generates newly exposed core 14' surfaces, to which the styrene acrylic resin (and other polymeric resin if present) adsorbs. The styrene acrylic resin 16 thus aids in dispersing the thioxanthone derivative photoinitiator cores 14' throughout the formulation. Together, the adsorbed resin 16 and the photoinitiator core 14 form the styrene acrylic resin stabilized thioxanthone derivative photoinitiator particles 17.

After the mixture has been thoroughly milled, the aqueous dispersant formulation may be removed from the bead mill mixer 12.

The aqueous dispersant formulation that is formed is transparent. This may be due, at least in part, to the formation of the styrene acrylic resin stabilized thioxanthone derivative photoinitiator particles 17, which are very small and dispersed throughout the water 22. In this example of the method, to determine whether the aqueous formulation has been formed, the appearance of the mixture and formulation may be monitored during bead milling.

The lack of color of the aqueous dispersant formulation may be advantageous for ink compositions, because the dispersant formulation will not deleteriously affect the intended color of the ink composition. In an example then, the aqueous dispersant formulation may be used as a photoinitiator in a radiation curable aqueous ink composition.

Turning to FIGS. 2A-2D, another example of the method for manufacturing the aqueous dispersant formulation is shown. In this example of the method, the mixture may be formed in several steps. The mixture that is ultimately formed may include the initial thioxanthone derivative photoinitiator 14, the styrene acrylic resin 16, and a balance of water 22. It is to be understood that, while not shown in FIGS. 2A-2D, the resulting mixture may also include the other polymeric dispersant, the co-solvent, or combinations thereof in addition to the components noted above. It is to be understood that the mixture formed in this example of the method may include the same type and amount of each component as previously described in reference to FIGS. 1A-1B.

As noted above, the mixture in this example of the method may be formed in several steps. In particular, two different compositions may be prepared and then combined together to form the mixture.

Figures 2A, 2B:
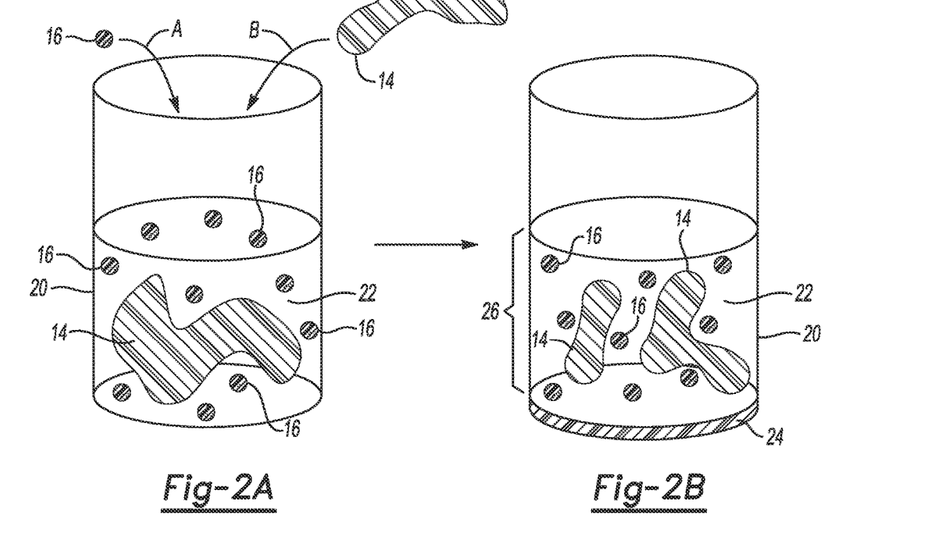
FIGS. 2A-2D are schematic, perspective and partially cross-sectional views of another example of a method for forming the aqueous dispersant formulation.

At reference letter A in FIG. 2A, the styrene acrylic resin 16 and the water 22 are mixed in a container 20. While not shown, in some instances, the other polymeric dispersant and/or the co-solvent may also be included with the styrene acrylic resin 16 and the water 22. In an example, any suitable container 20 may be used, such as a NALGENE® bottle.

The composition including at least the styrene acrylic resin 16 and the water 22 (referred to as the first composition) may then be heated. The temperature to which the first composition is heated may be within the same temperature range to which the second composition (which, as described below, includes the initial thioxanthone derivative photoinitiator 14) is heated. The first composition may be heated to a temperature ranging from about 40° C. to about 60° C. In an example, the first combination may be heated to about 50° C. The first composition may be heated by placing the container 20, which contains the first composition, into an oven that is set at a suitable temperature. The container 20 may be kept in the oven until the temperature of the first composition is about the temperature i) of the second composition or ii) to which the second composition is to be heated.

As indicated above, the second composition includes the initial thioxanthone derivative photoinitiator 14. It is to be understood that the initial thioxanthone derivative photoinitiator 14 is a water-insoluble photoinitiator that has a thick tree sap-like consistency and a dark color. In an example, the initial thioxanthone derivative photoinitiator 14 may be heated to a suitable temperature that will reduce the viscosity of the initial thioxanthone derivative photoinitiator 14 to equal to or less than 1000 cP. For example, the reduced viscosity may be in a range from about 500 cP to about 1000 cP.

Since it is desirable to achieve a workable viscosity of the second composition and to have the first and second compositions at similar temperatures, the heating temperature for both the first and second compositions will depend upon the initial thioxanthone derivative photoinitiator 14 that is used. In an example, the second composition (i.e., the initial thioxanthone derivative photoinitiator 14) is heated to a temperature ranging from about 40° C. to about 60° C. prior to being added to the first composition or having the first composition added thereto. In an example, the second composition is heated to about 50° C.

It is to be understood that the first and second compositions may be prepared sequentially (e.g., first and then second, or second and then first) or simultaneously. If prepared sequentially, whichever of the first and second compositions is prepared first in time may be maintained at the heated temperature (e.g., in an oven) until the other of the compositions (i.e., the second or the first) is prepared and heated.

When both the first and second compositions are at the selected temperature, the second composition (i.e., the initial thioxanthone derivative photoinitiator 14) may be added to the container 20 with the heated first composition. The addition of the second composition to the first composition is identified at reference letter B in FIG. 2A.

The combination of the first and second compositions forms the mixture. The mixture may be agitated (i.e., shaken, stirred, etc.) by hand or with a mechanical mixer until the mixture is uniformly mixed (as observed by the human eye).

The mixture may be placed in an oven to maintain the temperature of the mixture (e.g., at about 40° C. to about 60° C.). Following the example above, the oven may be heated to a temperature of about 50° C. to maintain the temperature of the mixture at about 50° C. The mixture may be maintained in the oven for a time ranging from about 6 hours to about 18 hours. As another example, the mixture may be maintained in the oven for a time ranging from about 6 hours to about 12 hours.

As shown in FIG. 2B, allowing the mixture to rest enables a sediment 24 (which may be dark in color) to form at the bottom of the container 20 and an aqueous supernatant 26 to form over the sediment 24. In an example, the sediment 24 contains a small percentage (e.g., 10% or less) of the initial thioxanthone derivative photoinitiator 14. The aqueous supernatant 26 includes the rest of the initial thioxanthone derivative photoinitiator 14, the styrene acrylic resin 16, a balance of water 22, and in some instances, the other polymeric dispersant and/or the co-solvent. The aqueous supernatant 26 may exhibit a translucent yellow color.

Figure 2C:
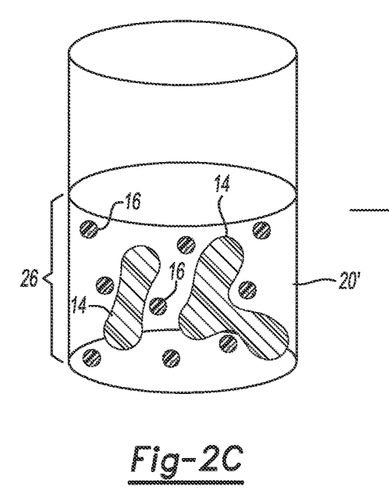

In this example of the method, the supernatant 26 may be decanted from the container 20 into another container 20' to separate the supernatant 26 from the sediment 24. Any other suitable separation technique may be used to separate the supernatant 26 from the sediment 24. For example, vacuum filtration may be used. The separated supernatant 26 in the container 20' is shown in FIG. 2C.

Figure 2D:
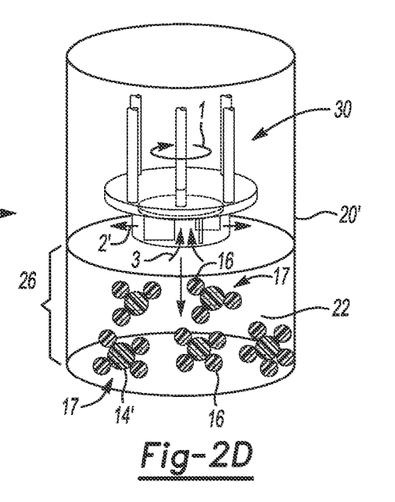

As shown in FIG. 2D, a high shear miller 30 may be positioned in the supernatant 26, or the supernatant 26 may be positioned in the high shear miller 30. Any suitable high shear miller 30 may be used. For examples, the high shear miller 30 may be a rotor-stator, such as a Silverson L5MA rotor-stator (made by Silverson) or the high shear miller 30 may be a grinding mill and dispersion machine, such as those manufactured by Kotobuki Industries. Other high shear millers 30 may be used, such as those available from Ross.

The supernatant 26 may be subjected to high shear milling until the aqueous dispersant formulation has been formed. The aqueous dispersant formulation is formed when the initial thioxanthone derivative photoinitiator 14 is reduced to form the cores 14', and the cores 14' are dispersed by the styrene acrylic resin 16 to form the styrene acrylic resin stabilized thioxanthone derivative photoinitiator particles 17 (each of which has a volume-weighted mean diameter of less than 40 nm).

To determine whether the aqueous dispersant formulation has been formed, the volume-weighted mean diameter of the photoinitiator 14, 14' and/or the appearance of the supernatant 26 may be monitored during milling. In an example, the volume-weighted mean diameter may be monitored by taking a sample during the milling process, analyzing the particle size/diameter of the sample, and calculating the volume-weighted mean diameter using the particle size/diameter. For example, a sample may be analyzed using a NANOTRAC® particle sizing system (which uses dynamic light scattering and is commercially available from Microtrac, Inc.), and then an algorithm (see, e.g., FIG. 4) may be used to calculate the volume-weighted mean diameter. When the average volume-weighted mean diameter is less than 40 nm, it can be determined that the aqueous dispersant formulation has been formed. Also during milling, the supernatant 26 transitions from being translucent yellow to being transparent when the aqueous dispersant formulation is formed. As such, the appearance may be monitored visually.

In an example, the high shear milling may be accomplished for a time ranging from about 30 minutes to about 90 minutes. In another example, the high shear milling may be accomplished for a time ranging from about 45 minutes to about 60 minutes.

In an example, the high shear miller 30 uses a suction force (shown as "3" in FIG. 2D) to draw the supernatant 26 from the bottom of the container 20' into the center of the workhead of the high shear miller 30. A centrifugal force (shown as "2" in FIG. 2D) caused by the rotation of the rotor (shown as "1" in FIG. 2D) causes the supernatant 26 to move towards the periphery of the workhead. The supernatant 26 may then be subjected to milling between the ends of the rotor blades and the inner wall of the stator. The centrifugal force also drives the supernatant 26 outward through perforations in the stator causing a hydraulic shear of the supernatant 26. After the supernatant 26 passed through the perforations, the supernatant 26 is circulated back into the mixture in the bottom of the container 20'.

During high shear milling, the photoinitiator 14 is broken up to form the photoinitiator cores 14', and the styrene acrylic resin 16 (and other polymeric resin if present) adsorbs to the cores 14' to form the styrene acrylic resin stabilized thioxanthone derivative photoinitiator particles 17.

After the supernatant 26 has been thoroughly milled to include the water dispersible styrene acrylic resin stabilized thioxanthone derivative photoinitiator particles 17, the transparent aqueous dispersant formulation is formed. In an example, the transparent aqueous dispersant formulation may be used as a polymeric photoinitiator in an aqueous ink composition (e.g., a radiation curable ink composition).

Examples of the transparent aqueous dispersant formulation disclosed herein may be present in the aqueous ink composition in an amount ranging from about 0.1 wt % active to about 1 wt % active based on the total wt % of the aqueous ink composition. As an example, the aqueous dispersant formulation may make up from about 0.1 wt % active to about 0.5 wt % active of the total wt % of the aqueous ink. This weight percentage accounts for the weight percent of active styrene acrylic resin stabilized thioxanthone derivative photoinitiator particles 17 present in the ink composition, and does not account for the total weight percent of the dispersant formulation. For example, this weight percentage does not account for water that may be present in the dispersant formulation.

In addition to the aqueous dispersant formulation disclosed herein, an example of the aqueous ink composition may also include a colorant, a radiation curable polyurethane dispersion, a co-solvent (in addition to water that is present as the main solvent), a surfactant, an anti-kogation agent, and water. In some examples, the aqueous ink composition may consist of these components and no other components. In yet another example, the aqueous ink composition may also include an additive(s) and/or a sensitizer.

The co-solvent(s) may be present in the aqueous ink composition in an amount ranging from about 1 wt % to about 15 wt % of the total wt % of the ink composition. In an example, the co-solvent is present in the aqueous ink composition in an amount ranging from about 3 wt % to about 10 wt % based on the total wt % of the aqueous ink composition. It is to be understood that other amounts outside of this example and range may also be used. Classes of co-solvents that may be used include organic co-solvents, such as aliphatic alcohols, aromatic alcohols, diols, glycol ethers, polyglycol ethers, 2-pyrrolidinones, caprolactams, formamides, acetamides, glycols, and long chain alcohols. Examples of these co-solvents include primary aliphatic alcohols, secondary aliphatic alcohols, 1,2-alcohols, 1,3-alcohols, 1,5-alcohols, ethylene glycol alkyl ethers, propylene glycol alkyl ethers, higher homologs ($C_6$-$C_{12}$) of polyethylene glycol alkyl ethers, N-alkyl caprolactams, unsubstituted caprolactams, both substituted and unsubstituted formamides, both substituted and unsubstituted acetamides, and the like. In some examples, the co-solvent may include 1-(2-hydroxyethyl)-2-pyrrolidone.

As mentioned above, examples of the aqueous ink composition may also include surfactant(s). As an example, the aqueous ink composition may include non-ionic, cationic, and/or anionic surfactants, which may be present in an amount ranging from about 0.01 wt % to about 2 wt % based on the total wt % of the aqueous ink composition. As an example, the surfactant amount may range from 0.5 wt % to about 1 wt % of the total wt % of the aqueous ink composition. In at least some examples, the surfactant may be SURFYNOL® CT-211 (now CARBOWET® GA-211, non-ionic, alkylphenylethoxylate and solvent free), SURFYNOL® 465 (ethoxylated acetylenic diol), and SURFYNOL® 104 (non-ionic wetting agent based on acetylenic diol chemistry) (all of which are from Air Products and Chemicals, Inc.). Other suitable surfactants may include a silicone-free alkoxylated alcohol surfactant such as, for example, TEGO® Wet 510 (Evonik Tego Chemie GmbH) and/or a self-emulsifiable wetting agent based on acetylenic diol chemistry, such as, for example, SURFYNOL® SE-F (Air Products and Chemicals, Inc.). Other suitable commercially available surfactants include; ZONYL® FSO (a.k.a. CAPSTONE®, which is a water-soluble, ethoxylated non-ionic fluorosurfactant from Dupont); TERGITOL® TMN-3 and TERGITOL® TMN-6 (both of which are branched secondary alcohol ethoxylate, non-ionic surfactants), and TERGITOL® 15-S-3, TERGITOL® 15-S-5, and TERGI- TOL® 15-S-7 (each of which is a secondary alcohol ethoxylate, non-ionic surfactant) (all of the TERGITOL® surfactants are available from The Dow Chemical Co.).

The aqueous ink composition may include the anti-kogation agent. Kogation refers to the deposit of dried ink on a heating element of a thermal inkjet printhead. Anti-kogation agent(s) is/are included to assist in preventing the buildup of kogation. Examples of suitable anti-kogation agents include oleth-3-phosphate (commercially available as CRODAFOS® O3A or CRODAFOS® N-3 acid from Croda Int.) or dextran 500k. Other suitable examples of the anti-kogation agents include CRODAFOS™ HCE (phosphate-ester from Croda Int.), CRODAFOS® N10 (oleth-10-phosphate from Croda Int.), or DISPERSOGEN® LFH (polymeric dispersing agent with aromatic anchoring groups, acid form, anionic, from Clariant), etc. The anti-kogation agent may be present in the aqueous ink composition in an amount ranging from about 0.05 wt % to about 2 wt % of the total wt % of the aqueous ink composition. As another example, the anti-kogation agent may be present in an amount ranging from about 0.5 wt % to about 1 wt %.

The aqueous ink composition may include a polyurethane. The polyurethane may be radiation curable, and may be part of a water-based dispersion. The polyurethane may be present in an amount ranging from about 1 wt % active to about 20 wt % active based on the total wt % of the aqueous ink composition. In another example, the polyurethane may be present in an amount ranging from about 5 wt % active to about 15 wt % active based on the total wt % of the aqueous ink composition. These weight percentages account for the weight percent of active polyurethane present in the aqueous ink composition, and do not account for the total weight percent of other components of water-based dispersion containing the polyurethane. For example, the polyurethane may be a 10% solution of the polyurethane in water, and thus 85 wt % of the polyurethane-containing dispersion would include 8.5 wt % active polyurethane.

In some examples, the aqueous ink composition may also include a sensitizer. As an example, a hydrogen donor sensitizer, such as a tertiary amine, may be used. In the ink includes another photoinitiator (e.g., a solid, acyl phosphine oxide photoinitiator, such as IRGACURE® TPO from BASF Corp.), the aqueous dispersant formulation disclosed herein may be used as the sensitizer. The sensitizer may be present in the aqueous ink composition in an amount ranging from 0 wt % to about 1.0 wt % active of the total wt % of the aqueous ink composition. In another example, the sensitizer is present in the aqueous ink composition in an amount of about 0.25 wt % active. The sensitizer may include other components, and thus this weight percentage accounts for the weight percent of active sensitizer present in the aqueous ink composition.

In some examples disclosed herein, the aqueous ink composition may also include antimicrobial agent(s) (biocide(s)), viscosity modifier(s), material(s) for pH adjustment, sequestering agent(s), preservative(s), jettability additive(s) (e.g., liponic ethylene glycol (LEG-1), available from Liponics), and the like. In an example, each of the additives may be present in the aqueous ink composition in an amount ranging from about 0.01 wt % to about 2 wt % based on the total wt % of the aqueous inkjet ink. In an example, the aqueous ink composition includes about 1 wt % of LEG-1.

The aqueous ink composition may be any color, such as black, cyan, magenta, yellow, etc. As such, in addition to the other components, the aqueous ink composition also includes a colorant. In an example, the colorant is a self-dispersed pigment. In another example, the colorant is a pigment in a dispersion including water, the pigment, and a polymer that disperses the pigment. In an example, the pigment dispersion may also include, for example, a co-solvent, such as 2-pyrrolidone. The pigment dispersion may be prepared or purchased, and the other components of the ink may be slowly added to the pigment dispersion with continuous mixing, to form the aqueous ink composition.

As used herein, "pigment" may generally include organic or inorganic pigment colorants, magnetic particles, aluminas, silicas, and/or other ceramics, organo-metallics, metallic particulates, or other opaque particles that introduce color to the ink composition. The pigment may be any color, including, as examples, a cyan pigment, a magenta pigment, a yellow pigment, a black pigment, a violet pigment, a green pigment, a brown pigment, an orange pigment, a purple pigment, a white pigment, a metallic pigment (e.g., a gold pigment, a bronze pigment, a silver pigment, or a bronze pigment), a pearlescent pigment, or combinations thereof. The total amount of pigment in the aqueous ink composition may range from about 2.5 wt % to about 5 wt % based on the total wt % of the aqueous ink composition.

To further illustrate the present disclosure, examples are given herein. It is to be understood that these examples are provided for illustrative purposes and are not to be construed as limiting the scope of the present disclosure.

EXAMPLES

Example 1

Several examples of the aqueous dispersant formulation disclosed herein were prepared. Each of the mixtures used to form the example aqueous dispersant formulations included GENOPOL*® TX-1 as the initial thioxanthone derivative photoinitiator, a different styrene acrylic dispersant, and a balance of water.

The styrene acrylic dispersants used in the mixtures are shown in Table 1. Several properties of the styrene acrylic dispersants used in the aqueous dispersant formulations are also provided in Table 1. The aqueous dispersant formulation (mixture) ID number (ID #), the particular styrene acrylic dispersant used (noting that styrene acrylic resins #1-5 are not commercially available), the acid number (AN) of the particular styrene acrylic dispersant used, and the weight-average molecular weight ($M_w$) of the particular styrene acrylic dispersant used are shown in Table 1.

TABLE 1

| ID # | Dispersant | AN [mg KOH/g resin] | $M_w$ [g/mol] |
|---|---|---|---|
| 1 | Styrene acrylic resin #1 | 140 | 6800 |
| 2 | Styrene acrylic resin #2 | 126 | 16500 |
| 3 | Styrene acrylic resin #3 | 205 | 8500 |
| 4 | Styrene acrylic resin #4 | 107 | 4500 |
| 5 | Styrene acrylic resin #5 | 200 | 13500 |
| 6 | JONCRYL ® 690 | 240 | 16500 |
| 7 | JONCRYL ® 680 | 215 | 4500 |

An example of the aqueous dispersant formulation was prepared as follows:

The mixture was formed using GENOPOL*® TX-1 as the initial thioxanthone derivative photoinitiator. The GENOPOL*® TX-1 was heated to 60° C. to reduce the viscosity. The heated GENOPOL*® TX-1 was then added to one of the dispersants listed in Table 1 in an amount of about 15 wt % based on the total weight percent of the mixture. The remainder (85 wt %) of each mixture included the respective styrene acrylic dispersant. Each styrene acrylic dispersant included the styrene acrylic resin and a balance of water, where the styrene acrylic resin was fixed at 8.5% actives.

Figure 3:
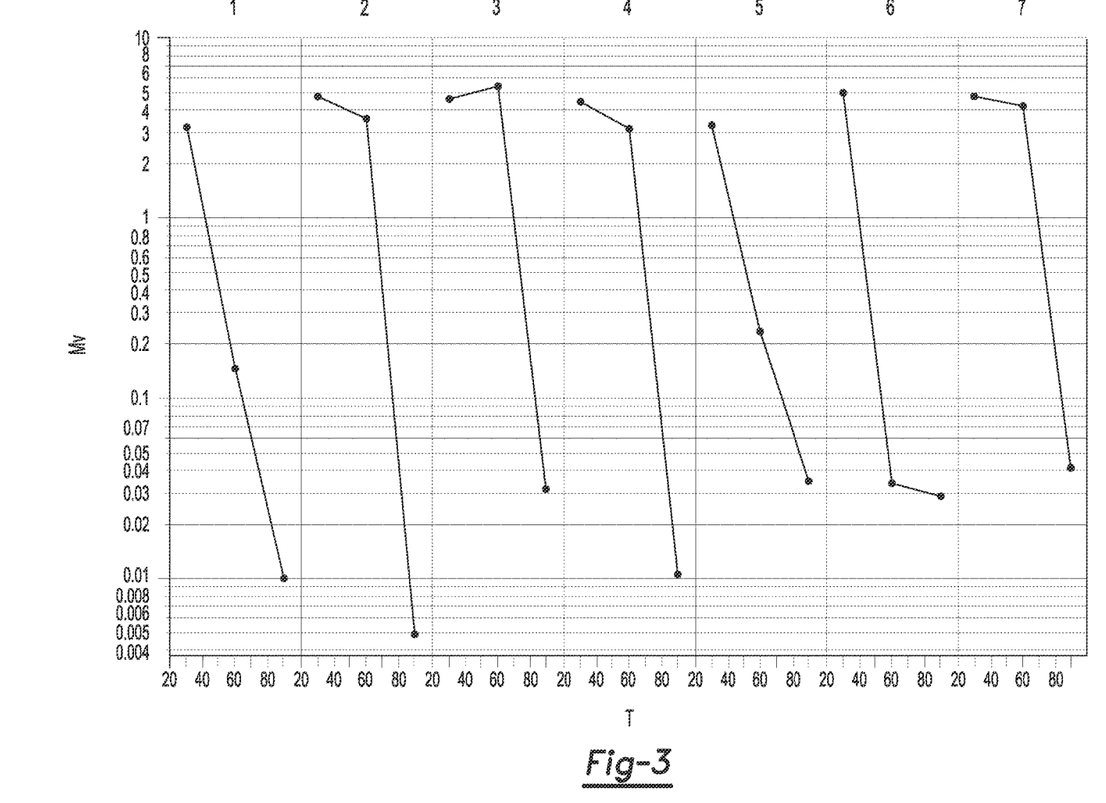
FIG. 3 is a graph of the change in volume-weighted mean diameter over bead milling time for examples of the aqueous dispersant formulation formed from an example of the method disclosed herein.

The mixture was bead milled in a Disperser DAS® 200 made by Lau for 1.5 hours (90 minutes) using 0.65 mm YTZ beads. Throughout bead milling, the particle size reduction for each example was monitored. In particular, the volume-weighted mean diameter of the photoinitiator, as it transformed into the styrene acrylic resin stabilized thioxanthone derivative photoinitiator particles, was determined. A sample of each example mixture or formulation was taken after 20 minutes of bead milling, after 60 minutes of bead milling, and (i.e., after the 90 minutes), and the particle size was measured. The particle size reduction is shown in FIG. 3 as the volume-weighted mean diameter (μm) (Y axis labeled "$M_v$") versus the bead milling time (minutes) (X axis labeled "T"). In FIG. 3, the aqueous dispersant formulations are listed by their ID # provided in Table 1.

Figure 4:
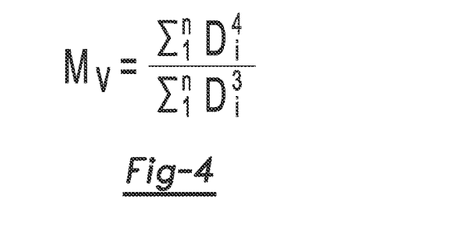
FIG. 4 depicts an example equation for determining volume-weighted mean diameter ($M_v$).

The volume-weighted mean diameter measurement is the mean diameter of the photoinitiator particles and/or the styrene acrylic resin stabilized thioxanthone derivative photoinitiator particles within a specific volume. The volume-weighted mean diameter is sometimes called the de Brouckere mean diameter, and is the weighted average volume diameter, assuming spherical particles of the same volume as the actual particles. FIG. 4 shows an example of a mathematical definition of volume-weighted mean diameter ($M_v$).

In this example, the volume-weighted mean diameter was measured with a NANOTRAC® 150 particle sizing system (using a 50% cumulative value of a volume-weighted mean diameter), commercially available from Microtrac, Inc. The particle sizing system uses dynamic scattering of laser light. The test samples for the NANOTRAC® 150 were prepared by diluting the samples (extracted after 20 minutes, 60 minutes, or 90 minutes of bead milling) [1:5000] with deionized water and analyzing the samples at ambient conditions without further treatment. If a concentrated dispersion is tested, the samples are diluted 1:10,000 times with deionized water and analyzed at ambient conditions without further treatment. As used herein, ambient conditions are defined as a temperature of 298.15 K (25° C., 77° F.) and an absolute pressure of 100 kPa (14.504 psi, 0.987 atm).

The results shown in FIG. 3 illustrate that the photoinitiator (as it transitioned from the initial state to the dispersant-stabilized thioxanthone derivative photoinitiator particles) in each of the mixtures or formulations had a significant reduction in volume-weighted mean diameter after 90 minutes of bead milling. The results in FIG. 3 also demonstrate that the initial thioxanthone derivative photoinitiator was broken, dispersed and stabilized after the formation of each aqueous dispersant formulation.

After each aqueous dispersant formulation was prepared, each formulation was tested for stability. One example for determining the stability of the dispersant formulations is to measure the volume-weighted distribution of the styrene acrylic resin stabilized thioxanthone derivative photoinitiator particles (particles 17). Such a distribution represents the population of particles, seen by their volume.

As mentioned above, the volume-weighted mean diameter measurement is the mean diameter of the dispersant-stabilized thioxanthone derivative photoinitiator particles within a specific volume, and FIG. 4 shows an example of a mathematical definition of volume-weighted mean diameter ($M_v$).

As an example, consider a representative sample taken from a large volume that only has 3 particles with diameters 1, 2, and 3. Applying the equation of FIG. 4, the volume-weighted mean diameter is $(1^4+2^4+3^4)/(1^3+2^3+3^3)=98/36=2.72$. As seen in the example, the volume-weighted mean diameter is sensitive to the presence of larger particles. In other words, in the 3 particle example above, the volume-weighted mean diameter (2.72) is closest to the largest diameter of 3. As such, if a large amount of flocculation occurs in the aqueous dispersant formulations, the volume-weighted mean diameter of the styrene acrylic resin stabilized thioxanthone derivative photoinitiator particles may increase over time when compared to the original measurement made after preparation of the aqueous dispersant formulations. Without being bound to any theory, the aqueous dispersant formulation particles exhibiting a small increase, no increase, or a decrease in volume-weighted mean diameter after accelerated storage conditions (discussed below in reference to Table 2) indicates that there is little or an acceptable amount of flocculation of the styrene acrylic resin stabilized thioxanthone derivative photoinitiator particles during storage. This is an indication that the aqueous dispersant formulation remains stable.

If after storage, the volume-weighted mean diameter remains relatively constant, this is an indication of a stable dispersion. However, if the volume-weighted mean diameter increases significantly after an aqueous dispersant formulation has been in storage, this may be a sign of undesirable flocculation and an indication of a less stable dispersion.

The formulations were prepared after 90 minutes of bead milling, and thus the volume-weighted mean diameter value measured at 90 minutes (see FIG. 3) was used as the value before the formulations were stored in an accelerated storage (AS) environment. Each aqueous dispersant formulation was re-measured after one week in the accelerated storage environment. The accelerated storage environment may be an environment that has a temperature ranging from about 45° C. to about 60° C. In this example, the accelerated storage environment was an oven baked at a temperature of about 60° C. The accelerated storage test results are shown below in Table 2. The change in the volume-weighted mean diameter is shown by $\Delta M_v$ in Table 2.

TABLE 2

| ID # | $M_v$ Before 1 Week AS (μm) | $M_v$ After 1 Week AS (μm) | $\Delta M_v$ (μm) |
| --- | --- | --- | --- |
| 1 | 0.010 | 0.086 | 0.076 |
| 2 | 0.005 | 0.010 | 0.005 |
| 3 | 0.032 | 0.075 | 0.043 |
| 4 | 0.011 | 0.067 | 0.056 |
| 5 | 0.035 | 0.006 | −0.029 |
| 6 | 0.042 | 0.015 | −0.027 |
| 7 | 0.029 | 0.027 | −0.002 |

In Table 2, the styrene acrylic resin stabilized thioxanthone derivative photoinitiator particle(s) exhibited a change in volume-weighted mean diameter that ranged from about −0.029 μm to about 0.076 μm after accelerated storage of the aqueous dispersant formulations for one week. The stability of the examples of the styrene acrylic resin stabilized thioxanthone derivative photoinitiator particle(s) disclosed herein is shown by the small change in the volume-weight mean diameter for formulations 1-4 and a decrease in the volume-weighted mean diameter for formulations 5-7. As such, these results show that the styrene acrylic resin stabilized thioxanthone derivative photoinitiator particle(s) are stable in the aqueous dispersant formulations over time.

In addition, in some of the examples, the results of Table 2 indicate that a styrene acrylic dispersant having a larger molecular weight and acid number may lead to more stable styrene acrylic resin dispersed thioxanthone derivative photoinitiator particle(s). For example, the styrene acrylic dispersant in formulations 5 and 6 had an acid number of at least 200 and a molecular weight of at least 13500 g/mol, and the styrene acrylic resin dispersed thioxanthone derivative photoinitiator particle(s) in these formulations exhibited a decrease in the volume-weighted mean diameter after one week in accelerated storage.

Example 2

In this example, several examples of the aqueous dispersant formulation disclosed herein were prepared. Each of the mixtures used to form the aqueous dispersant formulations has the same components, but they were exposed to different milling conditions as described below.

In this example, the aqueous dispersant formulations were prepared as follows:

GENOPOL*® TX-1 was used as the initial thioxanthone derivative photoinitiator. The GENOPOL*® TX-1 was heated to about 50° C. to reduce the viscosity to less than 1000 cP.

A separate vehicle was also prepared that included about 2 wt % active JONCRYL® 680 as the styrene acrylic dispersant, about 20 wt % active SOLSPERSE® 27000 as the other polymeric dispersant, about 10 wt % 1-(2-hydroxyethyl)-2-pyrrolidone (2HE2P) as a co-solvent, and a balance of water. The vehicle was also heated to about 50° C.

Once both the vehicle and the GENOPOL*® TX-1 were at 50° C., the GENOPOL*® TX-1 was then added to the vehicle to obtain the mixture. The mixture was then agitated by hand until it was uniformly mixed. The mixture was left undisturbed in an oven at 50° C. for about 12 hours.

The mixture was removed from the oven. About 10% of the mixture formed a dark solid sediment and the remaining aqueous portion of the mixture formed a supernatant. The supernatant was decanted to separate the supernatant from the solid sediment.

The supernatant was separated into three samples, which were then subjected to high shear milling (using different millers and/or different milling times) until the volume weighted mean diameter of resin stabilized thioxanthone derivative photoinitiator particles in each sample had an average volume weighted mean diameter of about 30 nm. The aqueous dispersant formulation ID number (ID #), the high shear miller used, and the milling time are shown in Table 3.

TABLE 3

| ID # | High Shear Miller | Time of Milling |
| --- | --- | --- |
| 8 | Kotobuki Mill | 60 Minutes |
| 9 | Silverson L5MA rotor-stator | 45 Minutes |
| 10 | Kotobuki Mill | 45 Minutes |

In order to demonstrate the effect of the initial heating, mixing, settling, and decanting on the initial thioxanthone derivative photoinitiator, a sample of the supernatant of example 8 prior to high shear milling, a sample of the dark solid sediment formed during the preparation of example 8, and a comparative sample of unprocessed (i.e., neat) GENOPOL*® TX-1 were each dissolved in tetrahydrofuran (THF). The samples were analyzed using a liquid chromatography-mass spectrometer (LCMS). The amount, based on the percentage of total GENOPOL*® TX-1 in each sample, of one, two, and three units in each sample was determined and is shown below in Table 4.

TABLE 4

| Sample | One unit | Two units | Three units |
| --- | --- | --- | --- |
| Comparative Unprocessed GENOPOL* ® TX-1 | 27 | 49 | 24 |
| Supernatant of Example 8 | 35 | 49 | 16 |
| Dark Solid Sediment of Example 8 | 4 | 42 | 54 |

Table 4 demonstrates that the initial preparation steps (i.e., heating, mixing, and allowing the mixture to rest in a heated oven) separate out the larger, three unit particles from the smaller one unit particles of the initial thioxanthone derivative photoinitiator. This is evidenced by the initial thioxanthone derivative photoinitiator consisting of 35% of one unit particles in the supernatant compared to 4% of one unit particles in the dark solid sediment, and the much higher percentage of three unit particles in the dark solid sediment.

A sample of each of the example aqueous dispersant formulations 8-10 was extracted and exposed to the same process, using the same equipment as described above to obtain the results shown in Table 5. A comparative sample was taken of the supernatant of example 8 prior to high shear milling. The samples of formulations 8-10 were taken after the high shear milling step was performed.

The percentage of each type of thioxanthone derivative photoinitiator particle present with one, two, or three units was determined based on the total wt % of the thioxanthone derivative photoinitiator in the final aqueous dispersant formulation. The results are shown in Table 5. The total wt % of the thioxanthone derivative photoinitiator in the aqueous dispersant formulation that was retained after high shear milling is also shown below in Table 5.

TABLE 5

| Sample | One subunit (wt %) | Two Subunits (wt %) | Three Subunits (wt %) | Total wt % |
| --- | --- | --- | --- | --- |
| Supernatant of Example 8 | 4 | 3.9 | 1.1 | 8.9 |
| 8 | 3.3 | 2.9 | 0.7 | 6.9 |
| 9 | 4.1 | 3.8 | 0.9 | 8.9 |
| 10 | 3.8 | 3.4 | 0.7 | 7.9 |

The results of Table 5 demonstrate an ability to produce the selective dispersion of the thioxanthone derivative photoinitiator by multiple processes. This is shown, in part, by the reduced wt % of the thioxanthone derivative photoinitiator three unit particles after each high shear milling technique (e.g., as compared to the Comparative Unprocessed GENOPOL*® TX-1 shown in Table 4). In all three examples 8-10, the wt % of the larger three subunit thioxanthone derivative photoinitiator particles was reduced. While the percentages of the one and two unit thioxanthone derivative photoinitiator particles were also reduced compared to the Comparative Unprocessed GENOPOL*® TX-1 shown in Table 4, the higher percentage of these types of particles compared to the three unit particles indicates that the particle size and volume weighted mean diameter were smaller.

The percent recovery of the thioxanthone derivative photoinitiator particles for example #2 in Table 1 of Example 1 and example #8 from Table 3 in Example 2 were also calculated to determine the yield of dispersant-stabilized thioxanthone derivative photoinitiator particles using each example method disclosed herein. These samples of example #2 and example #8 were prepared as previously described.

The percent recovery was determined by dividing the amount, in wt %, of thioxanthone derivative photoinitiator present in the final samples (i.e., after bead milling for Example #2 and after high shear milling for Example #8) by the amount, in wt %, of thioxanthone derivative photoinitiator present in the original mixtures, and multiplying by 100. In addition to the total percent recovery, the percent recovery of each particular unit was measured by diluting samples in tetrahydrofuran (THF) and using a liquid chromatography-mass spectrometer (LCMS) to measure the percent recovery. The results, in wt %, of the total thioxanthone derivative photoinitiator recovery and the recovery of each unit are shown in Table 6 below.

TABLE 6

| ID # | Total wt % Added to Formulation | Total wt % Found after Formation | % Recovery | % Recovery of One Subunit | % Recovery of Two Subunits | % Recovery of Three Subunits |
|---|---|---|---|---|---|---|
| 8 | 10 | 7.4 | 74 | 100 | 71 | 36 |
| 2 | 15 | 5.7 | 38 | 89 | 25 | 7 |

Table 6 shows that the high shear milling method, when compared to the bead mill method used in Example 1, increased the yield of the thioxanthone derivative photoinitiator particles in the aqueous dispersant formulation. In addition, the percent recovery of each of the subunits increased with the high shear milling of example #8 method when compared to the bead milling method of example #2. These results demonstrate that while both methods are useful for obtaining a water dispersible photoinitiator from a thick, water-insoluble photoinitiator, the high shear milling of the thioxanthone derivative photoinitiator particles may be a more efficient method of preparation (in terms of yield) compared to bead milling the thioxanthone derivative photoinitiator.

It is to be understood that the ranges provided herein include the stated range and any value or sub-range within the stated range. For example, a range from about 30 minutes to about 90 minutes should be interpreted to include not only the explicitly recited limits of about 30 minutes to about 90 minutes, but also to include individual values, such as 47.5 minutes, 49 minutes, 55 minutes, etc., and sub-ranges, such as from about 50 minutes to about 55 minutes, from about 57 minutes to about 60 minutes, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. An aqueous dispersant formulation, comprising:
   water; and
   styrene acrylic resin stabilized thioxanthone derivative photoinitiator particles dispersed in the water, the styrene acrylic resin stabilized thioxanthone derivative photoinitiator particles having a volume-weighted mean diameter of less than 40 nm, and including a water-insoluble, thioxanthone derivative photoinitiator core having one, two, or three units, wherein a structure of the unit is:

wherein x=2-12, and wherein when the water-insoluble, thioxanthone derivative photoinitiator core includes two units or three units, the units are covalently bonded together.

2. The aqueous dispersant formulation as defined in claim 1 wherein the formulation is transparent.

3. The aqueous dispersant formulation as defined in claim 1, further comprising an other polymeric dispersant.

4. The aqueous dispersant formulation as defined in claim 1, further comprising a co-solvent selected from the group consisting of 1-(2-hydroxyethyl)-2-pyrrolidone, 2-methyl-1,3-propanediol, 2-pyrrolidinone, dipropylene glycol methyl ether acetate, and combinations thereof.

5. The aqueous dispersant formulation as defined in claim 1 wherein a styrene acrylic resin of the styrene acrylic resin stabilized thioxanthone derivative photoinitiator particles has an acid number greater than or equal to 100 and a molecular weight greater than or equal to 4500 g/mol.

6. The aqueous dispersant formulation as defined in claim 1, further comprising 1-(2-hydroxyethyl)-2-pyrrolidone and a 100% active alkylphenol ethoxylate (APE) free polymeric dispersant.

7. A method for manufacturing an aqueous dispersant formulation, the method comprising:
   forming a mixture of a water-insoluble, thioxanthone derivative photoinitiator, a styrene acrylic resin, and water, wherein:
   the water-insoluble, thioxanthone derivative photoinitiator includes one, two, or three units, wherein a structure of the unit is:

and x=2-12;
and when the water-insoluble, thioxanthone derivative photoinitiator includes two units or three units, the units are covalently bonded together; and
milling the mixture to form styrene acrylic resin stabilized thioxanthone derivative photoinitiator particles having a volume-weighted mean diameter of less than 40 nm.

8. The method as defined in claim 7 wherein the milling is accomplished via bead milling for a time ranging from about 0.5 hours to about 1.5 hours.

9. The method as defined in claim 7 wherein prior to forming the mixture, the method further comprises:
heating the water-insoluble, thioxanthone derivative photoinitiator at a temperature ranging from about 40° C. to about 60° C. to reduce a viscosity of the water-insoluble, thioxanthone derivative photoinitiator to less than 1000 cP; and
heating the styrene acrylic resin and the water to the temperature of the heated water-insoluble, thioxanthone derivative photoinitiator.

10. The method as defined in claim 9, wherein forming the mixture is accomplished after the heating steps, and wherein the method further comprises:
allowing the mixture to sit in an environment at a temperature ranging from about 40° C. to about 60° C., thereby forming a sediment and a supernatant;
decanting the supernatant; and
wherein the milling of the mixture is accomplished by high shear milling the supernatant.

11. The method as defined in claim 10 wherein the high shear milling is accomplished for a time ranging from about 30 minutes to about 90 minutes.

12. The method as defined in claim 10, further comprising monitoring a volume-weighted mean diameter of the water-insoluble, thioxanthone derivative photoinitiator during the high shear milling.

13. The method as defined in claim 7 wherein the forming of the mixture further includes adding an other polymeric dispersant, a co-solvent, or combinations thereof to the water-insoluble, thioxanthone derivative photoinitiator, the styrene acrylic resin, and the water.

14. A method for manufacturing an aqueous dispersant formulation, the method comprising:
heating a water-insoluble, thioxanthone derivative photoinitiator at a temperature ranging from about 40° C. to about 60° C. to reduce a viscosity of the water-insoluble, thioxanthone derivative photoinitiator to less than 1000 cP, wherein the water-insoluble, thioxanthone derivative photoinitiator includes one, two, or three units, and a structure of the unit is:

where x=2-12, and wherein when the water-insoluble, thioxanthone derivative photoinitiator includes two units or three units, the units are covalently bonded together;
heating a combination of a styrene acrylic resin and water to the temperature of the water-insoluble, thioxanthone derivative photoinitiator;
adding the water-insoluble, thioxanthone derivative photoinitiator to the combination to form a mixture;
shaking the mixture;
allowing the mixture to sit at a temperature ranging from about 40° C. to about 60° C., thereby forming a sediment and a supernatant;
decanting the supernatant; and
milling the supernatant to form styrene acrylic resin stabilized thioxanthone derivative photoinitiator particles having a volume-weighted mean diameter of less than 40 nm.

15. The method as defined in claim 14 wherein the combination further includes an other polymeric dispersant, a co-solvent, or combinations thereof.

\* \* \* \* \*

UNITED STATES PATENT AND TRADEMARK OFFICE
CERTIFICATE OF CORRECTION

PATENT NO. : 10,071,353 B2
APPLICATION NO. : 15/543194
DATED : September 11, 2018
INVENTOR(S) : Marcos A. Barreto Caban et al.

Page 1 of 1

It is certified that error appears in the above-identified patent and that said Letters Patent is hereby corrected as shown below:

On the Title Page

In Column 2, item (57), Abstract, Line 5, delete "photo initiator" and insert -- photoinitiator --, therefor.

In Column 2, item (57), Abstract, Line 7, delete "photo initiator" and insert -- photoinitiator --, therefor.

Signed and Sealed this
Twenty-third Day of July, 2019

Andrei Iancu
*Director of the United States Patent and Trademark Office*